(12) United States Patent
Conrad et al.

(10) Patent No.: US 7,172,649 B2
(45) Date of Patent: Feb. 6, 2007

(54) LEUCITE GLASS CERAMIC DOPED WITH NANOSCALE METAL OXIDE POWDER, METHOD FOR PRODUCING THE SAME, AND DENTAL MATERIALS AND DENTAL PRODUCTS FORMED THEREFROM

(75) Inventors: Thomas Conrad, Dortmund (DE); Gerhard Meyer, Alte Delogstrasse 26, 46483 Wesel (DE)

(73) Assignees: Gerhard Meyer, Wesel (DE); Chemichl AG, Vaduz (LI)

(*) Notice: Subject to any disclaimer, the term of this patent is extended or adjusted under 35 U.S.C. 154(b) by 55 days.

(21) Appl. No.: 10/748,086

(22) Filed: Dec. 30, 2003

(65) Prior Publication Data

US 2005/0034631 A1   Feb. 17, 2005

(30) Foreign Application Priority Data

Dec. 30, 2002  (DE) ............................... 102 61 717

(51) Int. Cl.
*C03C 10/10* (2006.01)
*A61K 6/02* (2006.01)

(52) U.S. Cl. .................. 106/35; 501/6; 501/2; 501/32; 501/69; 501/70; 501/72; 501/3; 501/4; 501/5; 501/7; 501/8; 501/9; 501/10

(58) Field of Classification Search ................ 106/35; 501/6, 32, 2, 69, 70, 72, 3, 4, 5, 7, 8, 9, 10
See application file for complete search history.

(56) References Cited

U.S. PATENT DOCUMENTS

| | | | | |
|---|---|---|---|---|
| 4,978,640 | A | * 12/1990 | Kelly | 501/32 |
| 5,698,019 | A | * 12/1997 | Frank et al. | 106/35 |
| 5,698,482 | A | 12/1997 | Frank et al. | 501/10 |
| 6,527,846 | B1 | 3/2003 | Beham | 106/35 |
| 2004/0121894 | A1* | 6/2004 | Brodkin | 501/16 |

FOREIGN PATENT DOCUMENTS

| | | |
|---|---|---|
| DE | 33 39 490 A1 | 5/1985 |
| EP | 231 773 A1 | 8/1987 |
| EP | 690 031 B1 | 1/1996 |
| WO | WO 00/10509 | 3/2000 |

OTHER PUBLICATIONS

"Monodispersed Metal (Hydrous) Oxides - A Fascinating Field of Colloid Science", Matijevic, Acc. Chem. Res., 1981, pp. 22-29.
Formation, Packing, and Sintering of Monodisperse $TiO_2$ Powders, Barringer et al., J. Am. Ceram. Soc. 1982, pp. C199-C201.
"Applications of Sol-Gel Methods for Glass and Ceramics Processing", Mackenzie, Ultrastructure Processing of Ceramics, Glasses and Composites, 1984, pp. 15-26.
"Synthesis and Characterization of Monosized Doped $TiO_2$ Powders", Fegley Jr. et al., J. Am. Ceram. Soc. 1984, pp. C113-C116.
"Preparation of Y-Doped Zirconia by Emulsion Technique", Rinn et al., Ceramic Powder Processing Science (Proceedings of the Second International Conference, Oct. 12-14, 1988, pp. 221-228.
"Herstellung Nanoskaliger Pulver Durch Thermische Synthese im Pulsationsreaktor", Begand et al., 1988, D-12-D-16.
"Einsatz des Pulsationsreaktors für die Stoffbehandlung in der Chemischen Industrie", Begand et al, 1988, pp. 746-749.
"Preparation of Monodisperse $ArO_2$ by the Microwave Heating of Zirconyl Chloride Solutions", Moon et al., J. Am. Ceram. Soc. 78[4], 1995, pp. 1103-1106.
"Synthesis, Characterization, and Processing of Monosized Ceramic Powders", Fegley et al., Mat., Res. Soc. Symp. Proc. vol. 32, 1984, pp. 187-197.

* cited by examiner

*Primary Examiner*—C. Melissa Koslow
(74) *Attorney, Agent, or Firm*—Marshall, Gerstein & Borun LLP

(57) ABSTRACT

The disclosure relates to a leucite glass ceramic doped with nanoscale metal oxide, to a doped leucite glass ceramic powder suitable for its production, to a method for producing the doped leucite glass ceramic, to its use as dental material, to a dental product containing it and to the use of the nanoscale metal oxide powders for the production of the doped glass ceramic or of the doped leucite glass ceramic powder.

22 Claims, No Drawings

LEUCITE GLASS CERAMIC DOPED WITH NANOSCALE METAL OXIDE POWDER, METHOD FOR PRODUCING THE SAME, AND DENTAL MATERIALS AND DENTAL PRODUCTS FORMED THEREFROM

BACKGROUND OF THE INVENTION

1. Field of the Invention

The invention relates to a doped leucite glass ceramic, to a doped leucite glass ceramic powder suitable for its production, to a method for the production of the doped leucite glass ceramic, to its use as dental material, to a dental product containing it and to the use of nanoscale metal oxide powders for the production of the doped glass ceramic or of the doped leucite glass ceramic powder.

2. Related Technology

Leucite glass ceramics are used particularly in dental technology for the production of dental products such as, for example, dentures, tooth posts or dental root constructions. These dental products are frequently made by means of pressing techniques. Here, a (leucite) glass ceramic powder is first melted in a furnace and then shaped under pressure to form cylinders normally weighing two grams. These cylinders are then pressed in a special pressing furnace into a mold made of a wax-like positive model that has been prepared by the dental technician. Thus, through the use of the so-called lost wax technique, an exact copy of the original wax model is made of glass ceramic.

Consequently, a glass ceramic powder that is to be used in this process has to be sufficiently malleable on the one hand and sufficiently viscous on the other hand in order to completely fill the space defined by the wax model. At the same time, it is desirable for the glass ceramics that are employed to have a high bend strength so that the dental products made of them can withstand especially mechanical stress and do not easily break or develop cracks.

Leucite glass ceramics are sufficiently malleable and viscous for processing in a pressing furnace. However, it is desirable to further improve their bend strength and fracture resistance so as to be able to impart dental products with better mechanical properties.

SUMMARY OF THE INVENTION

Therefore, it is an objective of the invention to provide a leucite glass ceramic whose bend strength and fracture resistance are improved in comparison to the prior-art leucite glass ceramics. Moreover, a leucite glass ceramic powder is to be provided from which a leucite glass ceramic with the desired properties can be made.

This objective is achieved by providing a doped leucite glass ceramic powder containing (a) a leucite glass ceramic powder and (b) a nanoscale metal oxide powder with a $d_{50}$ value of 1 nm to 300 nm. This leucite glass ceramic powder allows the production of a leucite glass ceramic according to the invention, containing (a) a leucite glass ceramic and (b) a nanoscale metal oxide with a $d_{50}$ value of 1 nm to 300 nm. A leucite glass ceramic doped in this manner has a much greater bend strength in comparison to undoped leucite glass ceramics, while retaining good malleability and viscosity. If commercially available metal oxide powder having a particle size in the micrometer range is used to dope the leucite glass ceramic instead of the nanoscale metal oxide powder having the indicated particle size, the bend strength of the commercially doped leucite glass ceramic at times even falls below that of the undoped leucite glass ceramic.

DETAILED DESCRIPTION OF THE INVENTION

The term "leucite glass ceramic" as employed in this disclosure refers especially to a glass ceramic that is made up substantially of the skeleton silicate leucite ($K[AlSi_2O_6]$), whereby the leucite can contain additional elements or element oxides such as, for example, Na, Ca, Ba, Ce, B, or Ti, or oxides thereof.

Leucite glass ceramic powders are produced, for example, by means of the method disclosed in International Patent Publication No. WO 00/10509, the entire disclosure of which is incorporated herein by reference but they can also be produced using other methods on the basis of starting materials (such as, for example, oxides) that form leucite.

As the product to be protected, the composition of the leucite glass ceramic (a) of the doped leucite glass ceramic according to the invention is, for example, as follows:

| | |
|---|---|
| $SiO_2$ | 63% to 71% by weight (relative to the total weight of the leucite glass ceramic powder (a)); |
| $Al_2O_3$ | 10% to 15% by weight; |
| $K_2O$ | 8% to 10% by weight; |
| $Na_2O$ | 3% to 8% by weight; |
| CaO | 1% to 3% by weight; |
| BaO | 0.2% to 2% by weight; |
| $CeO_2$ | 0.5 to 2% by weight; |
| $B_2O_3$ | 0.5% to 2% by weight; |
| $TiO_2$ | 0% to 1% by weight. |

The term "nanoscale metal oxide powder" refers to those metal oxide powders whose average particle size lies in the nanometer range. The particle size is normally determined by means of laser diffraction.

The use of metals oxides containing $ZrO_2$ as the doping agent for glass ceramics is known in the art. For instance, European Patent No. 690 031, the entire disclosure of which is incorporated herein by reference, discloses glass ceramics that have at least two crystal phases, among others $ZrO_2$ and $P_2O_5$. These, however, preferably are not leucite glass ceramics and the $ZrO_2$ doping take place directly in the glass melt.

In a preferred embodiment, the leucite glass ceramic (a) of the doped leucite glass ceramic according to the invention has the following composition:

| | |
|---|---|
| $SiO_2$ | 70% by weight (relative to the total weight of the leucite glass ceramic powder (a)); |
| $Al_2O_3$ | 10% by weight; |
| $K_2O$ | 10% by weight; |
| $Na_2O$ | 5% by weight; |
| CaO | 2% by weight; |
| BaO | 1% by weight; |
| $CeO_2$ | 1% by weight; |
| $B_2O_3$ and $TiO_2$ | 1% by weight. |

This is a commercially available leucite glass ceramic, namely K 13 A. By means of any suitable method, such a glass ceramic powder (a) and a nanoscale metal oxide powder (b) can be used to obtain the doped leucite glass ceramic according to the invention.

It is preferred that the doped leucite glass ceramic according to the invention contains the nanoscale metal oxide (b) in an amount of 1% to 80% by weight (relative to the total weight of the doped leucite glass ceramic), especially 30% to 70% by weight, particularly preferably about 60% by weight. These doped leucite glass ceramics can be made by any suitable method, on the basis of the corresponding amounts of leucite glass ceramic powder (a) and nanoscale metal oxide powder (b). Thus, they can be obtained by grinding the powder employing a dry and wet-grinding method and subsequently melting it at temperatures, for example, ranging from 1100° C. to 1200° C. [2012° F. to 2192° F.]. Here, the ground-up powders are heated to the desired sintering temperature and kept at this temperature for a fixed period of time, normally for about 5 minutes to 30 minutes, and subsequently cooled. The ceramic obtained in this manner can then be further processed into the desired dental product by the dental technician—as explained above or in European Patent Publication No. 231 773 A1, the entire disclosure of which is incorporated herein by reference.

In some embodiments of the invention, the nanoscale metal oxide (b) may be present in an amount of 1% to 80% by weight, especially 30% to 70% by weight, particularly preferably about 60% by weight (relative to the total weight of the doped leucite glass ceramic), in the doped leucite glass ceramic. In other preferred embodiments of the invention, the particle size of the nanoscale metal oxide (b) may lie between 10 nm and 200 nm, especially 20 nm and 100 nm, particularly preferably 30 nm and 60 nm, in the doped leucite glass ceramic. In a preferred embodiment of the invention, the nanoscale metal oxide (b) in the dopes leucite alass ceramic is $ZrO_2$. In some other preferred embodiments of the invention, the nanoscale metal oxide (b) in doped leucite glass ceramic is $ZrO_2$ that has been stabilized with 0.5 mole-% to 12-mole % (relative to the total amount of nanoscale metal oxide) of another metal oxide. In some other preferred embodiments of the invention, the other metal oxide is 7 mole-% to 12 mole-%. especially about 9 mole % of MgO or CaO or 1 mole-% to 5 Mole-%, especially about 3 mole-% of $Y_2O_3$. In some other preferred embodiments of the invention, the nanoscale metal oxide (b) in the doped leucite ceramic is made by means of a plasma synthesis method and has an above-average fraction of extremely small nano-particles <60 nm and accordingly a large active surface area.

It has also been found that the particle size of the nanoscale metal oxide powder (b), which is combined with the leucite glass ceramic powder (a) by means of any suitable method to yield the doped leucite glass ceramic according to the invention, preferably lies between 10 nm and 100 nm, especially between 20 nm and 70 mm, and especially preferably between about 30 nm and 60 nm.

In addition to $Al_3O_2$, $Li_2O$, $TiO_2$, ZnO, and $La_2O_3$, for example, especially zirconium dioxide ($ZrO_2$) is suitable as the nanoscale metal oxide powder, especially preferably with a particle size of 30 nm to 60 nm. The zirconium oxide can be present in unstabilized form or it can have been stabilized with another metal oxide, whereby the other metal oxide is preferably present in an amount of 0.5 mole-% to 12 mole-%, relative to the total amount of nanoscale metal oxide. Especially magnesium oxide (MgO) in an amount of 7 mole-% to 12 mole-%, especially about 9 mole-%, of MgO or yttrium trioxide ($Y_2O_3$) in an amount of 1 mole-% to 5 mole-%, especially about 3 mole-%, of $Y_2O_3$, have been found to be suitable stabilizers. Moreover, calcium oxide (CaO) in an amount of 7 mole-% to 12 mole-% especially about 9 mole-%, scandium oxide ($Sc_2O_3$), or cerium oxide ($CeO_2$) can be used as stabilizers. The doped leucite glass ceramics according to the invention with the highest bend strength are obtained with unstabilized ZrO2 as the metal oxide powder (b).

The nanoscale metal oxide powders used to produce the leucite glass ceramics according to the invention can be made by means of any suitable synthesis method. Thus, for instance, metal oxide powders can be made via various chemical routes by means of sol-gel synthesis. One method is the micro-emulsion technique set forth by G. Rinn and H. Schmidt in Ceramic Powder Processing Science (Proceedings of the Second International Conference, Oct. 12 to 14, 1988). Other possibilities are offered by Y. T. Moon, D. K. Kim, C. H. Kim in J. Am. Ceram. Soc., 78[4] 1103–106; J. D. Mackenzie in Ultrastructure Processing of Ceramics, Glasses and Composites, 1984, pp. 15–26; E. A. Barringer and H. K. Bowen in J. Am. Ceram. Soc., 1982, pp. 199–201; E. Matijevic in Acc. Chem. Res., 1981, pp. 22–29; Fegley and Barringer in Mat. Res. Soc. Proc., 1984, pp. 187–197. As an alternative, the metal salt sols can yield the nanoscale metal oxide powders by means of flame pyrolysis according to S. Begand and S. Ambrosius in DKG, pp. D12–D16, 1988 and in Chemie Ingenieur Technik [chemical engineering technology], pp. 746–749; 1988. Finally, the nanoscale metal oxide powders can also be made by means of a plasma synthesis method according to German Patent Publication DE 33 39 490 A1.

The entire respective disclosures of the foregoing documents are incorporated herein by reference.

Surprisingly, it has been found that especially the use of nanoscale $ZrO_2$ produced by means of plasma synthesis results in especially great increases in the bend strength of the doped leucite glass ceramics according to the invention. The best results here are achieved when about 60% by weight of unstabilized, $ZrO_2$ produced by means of plasma synthesis is used, whereby the malleability of the correspondingly doped leucite glass ceramic is retained.

When it comes to the desired increase in the bend strength, it has been found to be especially advantageous to chemically cure the doped leucite glass ceramics according to the invention after they have been produced, for example, in a pressing furnace, and after they have been sintered. In this curing process, the ceramic is exposed to a solution of a curing agent for a certain period of time, for example, 1 hour to 24 hours, especially 4 hours to 12 hours, preferably about 8 hours, at an elevated temperature, for instance, 200° C. to 800° C. [392° F. to 1472° F.], especially 300° C. to 600° C. [572° F. to 1112° F.], preferably 420° C. to 550° C. [788° F. to 1022° F.]. This curing agent is preferably an (aqueous) solution of a curing salt that is preferably selected from the group consisting of NaCl, $NaNO_3$, KCl, and $KNO_3$. As a result of this curing, the already considerably increased bend strength values of the leucite glass ceramics according to the invention can be further increased, in some cases, even doubled.

Due to their high bend strength and fracture resistance, the doped leucite glass ceramics according to the invention are very well-suited as dental materials. Moreover, they exhibit a good resistance to thermal shocks. Furthermore, they can be processed at temperatures below 1200° C. [2192° F.] for which especially the advantageous hot pressing method (lost wax method) in the viscous state is used to make dental products, as is known, for instance, from European Patent Publication 231 773 A1. Shaping conventional high-strength glass ceramics is often not possible at these low temperatures. It has also been found to be an advantage that the doped leucite glass ceramics according to the invention—in contrast to many conventional glass ceramics—do not react with the embedding compound that is used to make shaped dental products by means of hot pressing. This is a great advantage for the dental technician doing the processing work.

Finally, the doped leucite glass ceramics according to the invention adhere very well to high-strength pure $ZrO_2$ ceramics, which is particularly important for their use in dental technology. For example, it is possible to press a fitting leucite glass ceramic onto a high-strength $ZrO_2$ ceramic root post immediately after individual shaping—that is to say, as a function of the cavity in question. Thus, the $ZrO_2$ root post is firmly anchored onto the tooth and a further tooth reconstruction can then be undertaken.

The above-mentioned properties mean that the doped leucite glass ceramic according to the invention is also used as dental material or as a dental product shaped with it or else as a component of dental material or of a dental product shaped with it. Preferred dental products are tooth root restorations such as tooth root constructions or tooth root posts.

Below, the invention will be described in greater detail on the basis of several examples without the scope of the invention being restricted by these. The following examples contain preferred embodiments and advantageous refinements of the invention.

EXAMPLES

Preliminary Remarks

The materials used are commercially available or can be made by means of suitable production methods.

The particle sizes were determined by transmission electron microscopy (TEM); the specific surface areas were determined on the basis of Brunauer, Emmett, and Teller (BET) techniques, and the crystal phases were determined by X ray diffractometry (XRD).

Example 1

Production of Nanoscale ZrO2 Powders by Means of the Plasma Synthesis Method 1757 grams of $ZrCl_4$ and 190 grams of $YCl_3 \cdot 6H_2O$, stabilized with 3 mole-% of $Y_2O_3$, were reacted to form 1 kg of nanoscale $ZrO_2$, having had an average particle size of 50 nm and a specific surface area of 26±2 m²/g.

Characteristic properties of this $ZrO_2$ powder are compiled in Table 1.

TABLE 1

| No. | Stabilizer | Average particle size [nm] | Specific surface area [m²/g] | $ZrO_2$ crystal phases |
|---|---|---|---|---|
| 1 | — | 30 | 35 ± 5 | 25% monocline 75% tetragonal |
| 2 | 9 mole-% of MgO | 55 | 20 ± 2 | 10% monocline 90% tetragonal |
| 3 | 3 mole-% of $Y_2O_3$ | 50 | 26 ± 2 | 10% monocline 90% tetragonal |

Example 2

Production of Doped Leucite Glass Ceramics

The leucite glass ceramic powder K 13S and a nanoscale $ZrO_2$ powder from Example 1 were ground up for 24 hours in ethanol and mixed (powder amount: 100 g). In order to determine the three-point bend strength according to the dental ceramic standard EN ISO 6872, the powder mixture was used to make dental transverse rupture test bars (dimensions: 30×4×1.3 mm) in the Lectra Press dental pressing furnace made by the UGIN Company.

As a comparative sample, a transverse rupture test bar was made analogously of an undoped leucite glass ceramic powder K 13 S (heating rate: 60° C. [108° F.] per minute, final sintering temperature: 760° C. [1400° F.] and holding time at the final sintering temperature: 5 minutes), which yielded a bend strength of 107 MPa using Weibull statistics. All of the samples had an unpolished surface. The tested samples and their bend strengths are compiled in Table 2.

TABLE 2

| Sample | Nanoscale $ZrO_2$ acc. to Example 1 | Doping content [% by weight] | Heating rate [° C./° F. per minute] | Final sintering temperature [° C./° F.] | Holding time at final sintering temperature [minutes] | Bend strength [MPa] |
|---|---|---|---|---|---|---|
| A | 1 | 60 | 90/162 | 1150/2102 | 5 | 214 |
| B | 1 | 60 | 90/162 | 1150/2102 | 7 | 198 |
| C | 1 | 60 | 90/162 | 1150/2102 | 10 | 177 |
| D | 2 | 80 | 140/252 | 1150/2102 | 10 | 152 |
| E | 2 | 80 | 140/252 | 1150/2102 | 14 | 161 |
| F | 3 | 60 | 90/162 | 1150/2102 | 5 | 130 |
| G | 3 | 60 | 90/162 | 1150/2102 | 7 | 132 |

The strength-increasing effect of the doping with the nano-materials according to the invention is clearly demonstrable on the basis of the measured values for the bend strength in Table 2.

Surprisingly, it was found that, even with such a high doping, which corresponds to a change in the ratio of the matrix to the doping agent, the malleability of the material mixture is ensured.

Example 3

Adhesion of a Doped Leucite Glass Ceramic According to Example 2

A doped leucite glass ceramic according to Example 2 (Sample A) was subjected to chemical curing with KNO3

(heating rate: 5° C. [9° F.] per minute, holding time: 8 hours at 480° C. [896° F.], cooling rate: 3° C. [5.4° F.]). The cured doped leucite glass ceramic obtained in this manner had a bend strength of 437 MPa.

The invention claimed is:

1. A doped leucite glass ceramic powder, comprising
   (a) a leucite glass ceramic powder; and
   (b) a nanoscale metal oxide powder with a $d_{50}$ value of 1 nm to 200 nm.

2. A doped leucite glass ceramic, comprising
   (a) a leucite glass ceramic; and
   (b) a nanoscale metal oxide with a $d_{50}$ value of 1 nm to 200 nm.

3. The doped leucite glass ceramic according to claim 2, wherein the leucite glass ceramic has the following composition:

| | |
|---|---|
| $SiO_2$ | 70% by weight (relative to the total weight of the leucite glass ceramic (a)); |
| $Al_2O_3$ | 10% by weight; |
| $K_2O$ | 10% by weight; |
| $Na_2O$ | 5% by weight; |
| CaO | 2% by weight; |
| BaO | 1% by weight; |
| $CeO_2$ | 1% by weight; |
| $B_2O_3$ and $TiO_2$ | 1% by weight. |

4. The doped leucite glass ceramic according to claim 2, wherein the nanoscale metal oxide (b) is present in an amount of 1% to 80% by weight (relative to the total weight of the doped leucite glass ceramic).

5. The doped leucite glass ceramic according to claim 2, wherein the nanoscale metal oxide (b) is present in an amount of 30% to 70% by weight (relative to the total weight of the doped leucite glass ceramic).

6. The doped leucite glass ceramic according to claim 2, wherein the nanoscale metal oxide (b) is about 60% by weight (relative to the total weight of the doped leucite glass ceramic).

7. The doped leucite glass ceramic according to claim 2, wherein the particle size of the nanoscale metal oxide (b) lies between 10 nm and 200 nm.

8. The doped leucite glass ceramic according to claim 2, wherein the particle size of the nanoscale metal oxide (b) lies between 20 nm and 100 nm.

9. The doped leucite glass ceramic according to claim 2, wherein the particle size of the nanoscale metal oxide (b) lies between 30 nm and 60 nm.

10. The doped leucite glass ceramic according to claim 2, wherein the nanoscale metal oxide (b) is $ZrO_2$.

11. The doped leucite glass ceramic according to claim 2, wherein the nanoscale metal oxide (b) is $ZrO_2$ that has been stabilized with 0.5 mole % to 12 mole % (relative to the total amount of nanoscale metal oxide) of another metal oxide.

12. The doped leucite glass ceramic according to claim 11, wherein the other metal oxide is 7 mole-% to 12 mole-% of MgO or CaO or 1 mole-% to 5 mole-% of $Y_2O_3$.

13. The doped leucite glass ceramic according to claim 11, wherein the other metal oxide is about 9 mole-% of MgO or CaO or about 3 mole-% of $Y_2O_3$.

14. The doped leucite glass ceramic according to claim 2, wherein the nanoscale metal oxide (b) is made by means of a plasma synthesis method.

15. The doped glass ceramic according to claim 14, wherein the nanoscale metal oxide powder (b) has an above-average fraction of extremely small nano-particles <60 nm and accordingly a large active surface area.

16. The doped leucite glass ceramic according to claim 2, wherein the ceramic has been subjected to chemical curing after its production.

17. The doped leucite glass ceramic according to claim 2, wherein the chemical curing is carried out with a salt that is selected from the group consisting of NaCl, $NaNO_3$, KCl, and $KNO_3$.

18. A method for producing a doped leucite glass ceramic comprising a leucite glass ceramic and a nanoscale metal oxide with a $d_{50}$ value of 1 nm to 200 nm, comprising sintering the doped leucite glass ceramic powder according to claim 1.

19. The method according to claim 18, comprising chemically curing the leucite glass ceramic after sintering.

20. A dental material or a dental product comprising the doped leucite glass ceramic of claim 2.

21. A shaped dental product, comprising a leucite glass ceramic according to claim 2.

22. The doped leucite glass ceramic according to claim 2, wherein the leucite glass ceramic powder has the following composition:

| | |
|---|---|
| $SiO_2$ | 63% to 70% by weight (relative to the total weight of the leucite glass ceramic powder (a)); |
| $Al_2O_3$ | 10% to 15% by weight; |
| $K_2O$ | 8% to 105 by weight; |
| $Na_2O$ | 3% to 8% by weight; |
| CaO | 1% to 3% by weight; |
| BaO | 0.2% to 2% by weight; |
| $CeO_2$ | 0.5% to 2% by weight; |
| $B_2O_3$ and $TiO_2$ | 0.5% to 2% by weight, |
| $TiO_2$ | 0% to 1% by weight. |

* * * * *

UNITED STATES PATENT AND TRADEMARK OFFICE
CERTIFICATE OF CORRECTION

| | | |
|---|---|---|
| PATENT NO. | : 7,172,649 B2 | Page 1 of 1 |
| APPLICATION NO. | : 10/748086 | |
| DATED | : February 6, 2007 | |
| INVENTOR(S) | : Thomas Conrad et al. | |

It is certified that error appears in the above-identified patent and that said Letters Patent is hereby corrected as shown below:

On the title page at (75): The order of the names of the inventors should be as follows:

Gerhard Meyer, Alte Delogstrasse 26, 46483 Wesel (DE)
Thomas Conrad, Dortmund (DE)

Signed and Sealed this

Fourteenth Day of August, 2007

JON W. DUDAS
*Director of the United States Patent and Trademark Office*